US005750131A

United States Patent [19]

Wichert et al.

[11] Patent Number: 5,750,131
[45] Date of Patent: May 12, 1998

[54] IFOSFAMIDE LYOPHILIZATE PREPARATIONS

[75] Inventors: Burkhard Wichert, Bielefeld; Dieter Sauerbier, Oerlinghausen; Jurgen Rawert, Werther, all of Germany

[73] Assignee: Asta Medica Aktiengesellschaft, Dresden, Germany

[21] Appl. No.: 752,069

[22] Filed: Nov. 19, 1996

[51] Int. Cl.$^6$ .................. A61K 9/00; A61K 31/715
[52] U.S. Cl. .................. 424/422; 424/423; 514/54; 514/57; 514/59; 514/60; 514/110
[58] Field of Search .................. 424/422, 423, 424/464, 465; 514/54, 57, 59, 60, 110

[56] References Cited

U.S. PATENT DOCUMENTS

| | | | |
|---|---|---|---|
| 4,959,215 | 9/1990 | Sauerbier, et al. | 424/422 |
| 5,036,060 | 7/1991 | Alam et al. | 514/110 |
| 5,227,373 | 7/1993 | Alexander et al. | 514/110 |

FOREIGN PATENT DOCUMENTS

95/07083  9/1994  WIPO .

*Primary Examiner*—Joseph McKane
*Attorney, Agent, or Firm*—Cushman Darby & Cushman IP Group Of Pillsbury Madison & Sutro, LLP

[57] ABSTRACT

The invention relates to improved ifosfamide preparations which are distinguished in that as primary auxiliary a polysaccharide, in general a glycan, preferably dextran, starches or cellulose, in particular dextrans having an MW of 20.000 to 85.000, modified starches such as hydroxyethyl starch and chemically modified celluloses such as hydroxyethylcellulose and sodium carboxymethylcellulose, a glycol ether, preferably polyethylene glycol, in particular polyethylene glycols having a molecular weight of 600 to 6000 or an amino acid, preferably alanine, leucine or glutamic acid, is added to them.

The improved ifosfamide preparation can also contain as an auxiliary a pharmaceutically customary buffer, for example acetate, citrate or tris buffer, preferably phosphate buffer.

In addition, improved ifosfamide preparations are obtained by addition of NaHCO$_3$.

The ifosfamide preparations according to the invention can comprise one or a combination of several auxiliaries. Mesna can be added to the formulation as a uroprotector.

21 Claims, No Drawings

IFOSFAMIDE LYOPHILIZATE PREPARATIONS

BACKGROUND OF THE INVENTION

1. Field of the Invention

The invention relates to ifosfamide preparations having advantageous properties and in particular stability advantages compared with other ifosfamide lyophilizates described, and to processes for their preparation. They can be used in the pharmaceutical industry and in medicine.

2. Prior Art

Ifosfamide, an alkylating cytostatic of the oxazaphosphorine group, has the chemical name: 3-(2-chloroethyl)-2-(chloroethylamino)tetrahydro-2H-1,3,2-oxazaphosphorine-2-oxide.

The substance in its anhydrous form is a hygroscopic, white, crystalline powder having a melting point of 48° C. to 51° C. Ifosfamide tends to sinter below these temperatures.

This oxazaphosphorine was mentioned in addition to others in the patent by Arnold et al. (U.S. Pat. No. 3,732,340). Engel et al. (U.S. Pat. No. 4,882,452) describes a specially characterized crystalline ifosfamide and its preparation.

The solubility of ifosfamide is about 10% by weight in water, the aqueous solutions only being of limited shelf-life at room temperature. Sintered ifosfamide turns yellowish; at the same time the rate of dissolution of the product decreases. Ifosfamide solutions are administered parenterally at a maximum concentration of the aqueous solution of 4%.

On account of the physicochemical properties of ifosfamide outlined above, other administration forms besides the sterile crystallizate were patented.

Sauerbier et al. (U.S. Pat. No. 4,952,572) describe a non-aqueous concentrated ifosfamide solution which is diluted with water before use.

Various patents claim stable ifosfamide lyophilizates which were prepared with addition of auxiliaries. Thus the patent EP 265,812 by Sauerbier et al. is based on a lyophilizate consisting of ifosfamide-hexitol formulations. Of the hexitols, mannitol was preferred. In a further patent by Sauerbier et al. (U.S. Pat. No. 4,959,215), mesna, chemically the sodium salt of mercaptoethanesulphonic acid, was added to the above-described formulation as a uroprotector. In the patent by Alexander et al. (EP 0 538 858), an ifosfamide lyophilizate is mentioned in which urea is employed as a bulking agent. In combination with mesna as well, the formulation should lead to an acceptable product.

The investigations on which the present patent is based then surprisingly showed that as a result of the addition of polymeric auxiliaries or amino acids and inorganic salts stable ifosfamide lyophilizates can be obtained. The polymeric auxiliaries include the polysaccharide and the glycol ether groups.

This is remarkable, as, for example, in the patent by Sauerbier et al. (EP 3 628 369.2) it is shown that glycol ethers of the polyethylene glycol type together with oxazaphosphorines do not result in storable pharmaceutical preparations.

It is furthermore mentioned in the ifosfamide patent by Alexander et al. (EP 0 538 858) that lyophilizates which contain the amino acid glycine or the salt $NaHCO_3$ do not show favourable stability properties.

SUMMARY OF THE INVENTION

The oxazaphosphorine ifosfamide is the therapeutically active constituent of the formulations according to the invention. It is a widespread alkylating agent in cancer therapy.

The object was therefore to prepare an ifosfamide formulation in which the active agent has an acceptable stability and especially does not allow the unfavourable physicochemical properties of ifosfamide—hygroscopicity and tendency to sinter—to have an influence.

The development of freeze-drying products is a favourable route. Products are obtained in whose preparation the hygroscopicity of the active compound is not of importance.

The ifosfamide preparations described in this patent offer the desired favourable properties and unexpectedly also showed stability advantages compared with other ifosfamide lyophilizates described in patents.

The ifosfamide formulations according to the invention mentioned in this patent are based on studies which were carried out in order to find storage-stable solid ifosfamide preparations. Additions of auxiliary were used for this which had formerly not been described or had been described as unsuitable. To find suitable auxiliaries, the auxiliaries which are administrable parenterally were classified according to their chemical nature and assembled to give substance groups. From these groups, characteristic lead substances were in each case selected and ifosfamide lyophilizates prepared therewith.

The substance classes and the lead substances tested from them can be taken from the following table (Tab. 1):

TABLE 1

| Substance classes investigated and their lead substances | |
|---|---|
| Substance class | Lead substance |
| Monosaccharides: | |
| Aldohexoses | Glucose |
| | Galactose |
| Ketohexoses | Fructose |
| Disaccharides | Sucrose |
| Polysaccharides: | |
| Dextrans | Dextran |
| Starches | Hydroxyethyl starch |
| Alginates | Alginic acid |
| Celluloses | Hydroxyethylcellulose |
| | Hydroxypropylcellulose |
| | Sodium carboxymethylcellulose |
| Glycol ethers | Polyethylene glycol |
| Amino acids | Alanine |
| | Leucine |
| | Aspartic acid |
| | Glutamic acid |
| | Arginine |
| Buffers | Phosphate buffer |
| | Tris buffer |
| | Citrate buffer |
| | Acetate buffer |
| Others | Gelatine, $NaHCO_3$ |

Using the abovementioned lead substances, ifosfamide/auxiliary formulations were prepared, lyophilized and included in a storage test.

The lyophilizates were stored at room temperature for a period of 15 months. The samples were assessed before storage and after completion of storage.

As criteria for the assessment of the lyophilizates, various characteristics were used, such as, for example: the appearance characteristics of the lyophilizate cake with respect to structuring of the surface, shrinkage and appearance on thawing, the overall structure of the cake, its solidity, the crystallinity and the colour.

In particular, the discoloration of the lyophilizate cake to yellowish or brownish is a characteristic feature of decomposed ifosfamide.

The freeze-drying solutions contained the active compound in concentrations, for example, of between 1 and 10% by weight, preferably 4 to 10% by weight, in particular 10% by weight.

The auxiliary or the auxiliary combination was added to this solution in concentrations of between 0.1% by weight up to at most the amount needed for rendering the ready-to-use solution isotonic or up to the maximum solubility of the auxiliary in the freeze-drying solution.

The concentration of the ready-to-use solution is, for example, in the range between 0.1 and 4% by weight, preferably between 2 and 4% by weight, in particular 4% by weight.

If mesna is added to the product, this is contained in the lyophilizate in amounts from 0.1 to 1 part by weight per part by weight of ifosfamide.

The discovery of novel additions of auxiliary which lead to a stable ifosfamide lyophilizate was unexpected, as the substances mentioned are in part chemically reactive substances.

It is particularly remarkable that some of the auxiliaries present in the ifosfamide preparations according to the invention were beforehand described as unsuitable.

The formulations described according to the invention were prepared by dissolving the active compound including the auxiliary or the auxiliary combination in a suitable pharmaceutically acceptable solvent. Solvents which can be used are, for example, hydroalcohols, but preferably aqueous solutions are prepared.

The freeze-drying solution is dispensed under aseptic conditions after sterile filtration. Primary packings are customarily glass vials to which between 0.1 and 5 g of ifosfamide are added. The product is dried in a freeze-drying unit under adequate conditions to a residual moisture which does not affect the storage stability of the lyophilizate.

In the course of the investigations whose results are the basis of this patent, various active compound/auxiliary combinations were then prepared and representative samples included in the storage test.

Table 2 shows the results of the assessment after preparation and after 15-months' storage at room temperature:

TAB. 2

Description of various representative ifosfamide/auxiliary lyophilizates after preparation and after 15-months' storage at room temperature

| Auxiliary | t = 0 months (lyophilizate cakes) | | t = 15 months (lyophilizate cakes) | |
|---|---|---|---|---|
| | Description | Colour | Description | Colour |
| Alanine | solid, smooth | white | unchanged | unchanged |
| Carboxymethyl-cellulose-Na | solid, smooth | white | unchanged | unchanged |
| Hydroxyethyl starch | solid, smooth | white | unchanged | unchanged |
| Polyethylene glycol | solid, smooth | white | unchanged | unchanged |
| Dextran | solid, smooth | white | unchanged | unchanged |
| Glutamic acid | solid, smooth | white | unchanged | unchanged |
| NaHCO$_3$ | rough, sl. shr. | white | unchanged | unchanged |
| Phosphate | solid, rough, | white | unchanged | unchanged |

TAB. 2-continued

Description of various representative ifosfamide/auxiliary lyophilizates after preparation and after 15-months' storage at room temperature

| Auxiliary | t = 0 months (lyophilizate cakes) | | t = 15 months (lyophilizate cakes) | |
|---|---|---|---|---|
| | Description | Colour | Description | Colour |
| buffer | sl. shr. | | | |
| Leucine | fractured, n. solid | white | unchanged | unchanged |
| Hydroxyethyl-cellulose | solid, shr. | white | unchanged | unchanged |
| Hydroxypropyl-cellulose | solid, sl. shr | white | cryst., clear, shr. | yellowish |
| Aspartic acid | no cake | white | cryst., clear | yellowish |
| Sucrose | solid, shr., cryst. | white | cryst., clear, shr. | yellowish |
| Arginine | no cake | white | cryst., clear | yellowish |
| Tris buffer | solid, smooth, sl. shr. | white | cryst., clear, shr. | yellowish |
| Citrate buffer | no cake | clear | cryst., clear | yellowish |
| Acetate buffer | n. solid, smooth | white | cryst., shr. | yellowish |
| Gelatine | solid, smooth, shr. | white | shr. | lemon-yellow |
| Alginic acid | solid, sl. shr. | yellowish | sl. shr. | beige-brown |
| Galactose | no cake | white | cryst. | red-brown |
| Fructose | gel | clear | viscous | red-brown |

[Abbreviations: sl. shr. = slightly shrunk, n. = not, cryst. = crystalline]

As can be seen from the table, several formulations surprisingly show no changes after storage with respect to the appearance of the lyophilizate cake and especially with respect to the colour. No severe decomposition of ifosfamide occurred in these ifosfamide lyophilizates. The storage stability of formulations which contain corresponding auxiliaries is given.

This is to be emphasized in particular in the case of auxiliaries which were described beforehand as not suitable. Polyethylene glycol is to be mentioned here (Sauerbier et al. EP 3 628 369.2) and NaHCO$_3$ (Alexander et al.: EP 0 538 858).

With the aid of the investigations carried out, on the one hand novel storage-stable ifosfamide lyophilizate formulations were found, and on the other hand it was shown that stable lyophilizates can also be obtained with polyethylene glycol and NaHCO$_3$.

In the following, the preparation of the lyophilizates is described in detail with the aid of some non-limiting examples. Examples are not provided for all active compound/auxiliary combinations which have been mentioned above and for the various ifosfamide dosages. However, it is possible to prepare the formulations and dosages described according to the invention in this patent in a corresponding manner.

DETAILED DESCRIPTION OF PREFERRED EMBODIMENTS OF THE INVENTION

The invention is presented in greater detail with the aid of the following working examples without, however, restricting it thereto.

EXAMPLE 1

8 liters of water for injection purposes are initially introduced into a suitable vessel and 1000 g of ifosfamide and 337.3 g of alanine are dissolved therein. Using water for injection purposes, the solution is made up to a final volume of 10 liters. A sterile filtration unit using customary sterile filters (pore width 0.2 μm) follows. The sterile solution is dispensed under aseptic conditions into previously cleaned and sterilized 30 ml glass vials. The amount dispensed per vial is 10.0 ml. After cleaned and sterilized freeze-drying stoppers have been placed on the vials, the vials are transferred to a suitable freeze-drying unit and cooled to a temperature of −40° C.

In the following main drying phase, the product is warmed to about +15° C., the chamber being evacuated to a pressure of about 0.5 mbar. After a drying period of about 14–16 hours, the afterdrying phase is started, in which the plate temperature is raised to about +25° C. and the chamber pressure is lowered to a value below $1 \times 10^{-3}$ mbar. After about 4 hours, the unit is aerated with sterile-filtered media ($N_2$ or air). The vials are aseptically sealed in the chamber by lowering the positioning plates. After unloading the vials, these are provided with suitable crimped aluminium caps.

If a dosage other than the 1 g mentioned in this example is prepared, the vial size, the volume dispensed and the freeze-drying process are to be adjusted accordingly.

The ifosfamide dosages are customarily in a range from 100 mg to 5 g. The packings used for these dosages customarily have a volume of between 10 and 125 ml.

EXAMPLE 2

The formulation which was mentioned in Example 1 can contain additional auxiliaries such as buffers, other bulking agents or preservatives.

The total amount of additives is customarily set such that the reconstituted ready-to-use lyophilizate yields an almost isotonic solution.

The preparation of such a lyophilizate is identical to the preparation path presented in Example 1.

What is claimed is:

1. A lyophilized preparation, consisting of ifosfamide and 0.1 part by weight up to at most the amount of one or more amino acids needed for rendering a ready-to-use solution isotonic and, if appropriate, other customary pharmaceutical auxiliaries.

2. A lyophilized preparation according to claim 1, wherein the amino acid consists of alanine, glutamic acid or leucine.

3. A lyophilized preparation, consisting of ifosfamide and 0.1 part by weight up to at most the amount of one or more polysaccharides needed to render a ready-to-use solution isotonic and, if appropriate, other customary pharmaceutical auxiliaries.

4. A lyophilized preparation according to claim 3, wherein the polysaccharide consists of a dextran.

5. A lyophilized preparation according to claim 4, wherein the dextran has a molecular weight of 20,000 to 85,000 daltons.

6. A lyophilized preparation according to claim 3 wherein the polysaccharide consists of a starch.

7. A lyophilized preparation according to claim 6 wherein the starch consists of chemically modified starch.

8. A lyophilized preparation according to claim 3, wherein the polysaccharide consists of a cellulose.

9. A lyophilized preparation according to claim 8, wherein the cellulose is a chemically modified cellulose.

10. A lyophilized preparation consisting of ifosfamide and 0.1 part by weight up to at most the amount of one or more glycol ethers needed for rendering a ready-to-use solution isotonic and, if appropriate, other customary pharmaceutical auxiliaries.

11. A lyophilized preparation according to claim 10, wherein the glycol ether is a polyethylene glycol.

12. A lyophilized preparation according to claim 11, wherein the polyethylene glycol is a polyethylene glycol having a molecular weight from 600 to 6000 daltons.

13. A lyophilized preparation, consisting of ifosfamide and 0.1 part by weight up to at most the amount of one or more pharmaceutically customary buffer substances needed to render a ready-to-use solution isotonic and, if appropriate, other customary pharmaceutical auxiliaries.

14. A lyophilized preparation according to claim 13, wherein the buffer substance is a phosphate buffer.

15. A lyophilized preparation consisting of ifosfamide and 0.1 part by weight up to at most the amount of sodium hydrogen phosphate needed to render a ready-to-use solution isotonic and, if appropriate, other customary pharmaceutical auxiliaries.

16. A lyophilized preparation according to any one of claims 1, 3, 10, 13, and 15, wherein after reconstitution thereof the concentration of the ready-to-use solution is in the range between 0.1 and 4% by weight.

17. A lyophilized preparation according to any one of claims 1, 3, 10, 13, and 15, wherein 0.1 to 1 part by weight of mesna per part by weight of ifosfamide is present as pharmaceutical auxiliary.

18. A lyophilized preparation according to claim 7, wherein the starch consists of hydroxyethyl starch.

19. A lyophilized preparation according to claim 9, wherein the cellulose is hydroxyethylcellulose or sodium carboxymethyl cellulose.

20. A lyophilized preparation according to claim 16, wherein after reconstitution thereof the concentration of the ready-to-use solution is in the range between 2 and 4% by weight.

21. A lyophilized preparation according to claim 20, wherein after reconstitution thereof the concentration of the ready-to-use solution is 4% by weight.

* * * * *